United States Patent [19]

Sarrett

[11] Patent Number: 5,405,354
[45] Date of Patent: Apr. 11, 1995

[54] SUTURE DRIVER

[75] Inventor: David L. Sarrett, Virginia Beach, Va.

[73] Assignee: Vance Products Inc., Spencer, Ind.

[21] Appl. No.: 103,452

[22] Filed: Aug. 6, 1993

[51] Int. Cl.⁶ .......................................... A61B 17/00
[52] U.S. Cl. ................................ 606/148; 606/139;
606/223; 112/80.03; 112/169; 223/102; 163/5;
289/16
[58] Field of Search ............. 606/139, 144, 147, 148,
606/151, 205, 207–208, 222, 223; 604/158, 162,
164; 112/80.03, 169; 223/102, 104; 289/16;
163/5

[56] References Cited

U.S. PATENT DOCUMENTS

| D. 330,591 | 10/1992 | Rosenberg et al. | D24/147 |
|---|---|---|---|
| 2,363,334 | 11/1944 | Jones | 606/147 |
| 3,638,654 | 2/1972 | Akuba . | |
| 3,656,485 | 4/1972 | Robertson . | |
| 3,763,860 | 10/1973 | Clarke . | |
| 3,871,379 | 3/1975 | Clarke . | |
| 3,995,619 | 12/1976 | Glatzer . | |
| 4,602,635 | 7/1986 | Mulhollan et al. . | |
| 4,617,933 | 10/1986 | Hasson . | |
| 4,935,027 | 6/1990 | Yoon | 606/146 |
| 5,015,250 | 5/1991 | Foster | 606/147 |
| 5,059,201 | 10/1991 | Asnis | 606/144 |
| 5,100,418 | 3/1992 | Yoon et al. | 606/139 |
| 5,129,912 | 7/1992 | Noda et al. | 606/139 |
| 5,141,520 | 8/1992 | Goble et al. | 606/232 |
| 5,147,380 | 9/1992 | Hernandez et al. | 606/207 |
| 5,152,769 | 10/1992 | Baber | 606/145 |
| 5,196,022 | 3/1993 | Bilweis | 606/144 |
| 5,201,744 | 4/1993 | Jones | 606/148 |
| 5,222,977 | 6/1993 | Esser | 606/148 |
| 5,300,082 | 4/1994 | Sharpe et al. | 606/147 |

FOREIGN PATENT DOCUMENTS

| 0686926 | 8/1930 | France | 606/147 |
| 0712346 | 9/1931 | France | 606/144 |

Primary Examiner—Stephen C. Pellegrino
Assistant Examiner—Jeffrey A. Schmidt
Attorney, Agent, or Firm—Richard J. Godlewski

[57] ABSTRACT

A suture driver for clamping a suture in the hollow passage and a recessed channel thereof and manipulating the suture to and from a surgical site. The driver includes an outer member tube having a closed and pointed distal end for percutaneous introduction into the body of a patient. The outer tube also includes a recessed channel positioned proximal the closed distal end of the hollow passage extending longitudinally therein and for receiving the suture therein. An inner rod is positioned in the passage of the outer tube and has a clamping surface at the distal end thereof for engaging a suture positioned in the recessed channel. The inner rod is slid through the recessed channel to clamp the suture in the hollow passage of the outer tube against another clamping surface at the distal end of the tube. A handle positioned at the proximal end of the outer tube and inner rod is manipulated to slide the inner rod through the recessed channel and clamp the suture in the hollow passage between the two clamping surfaces. The inner rod positioned through the recessed channel also reinforces the outer tube during percutaneous introduction into the patient.

20 Claims, 2 Drawing Sheets

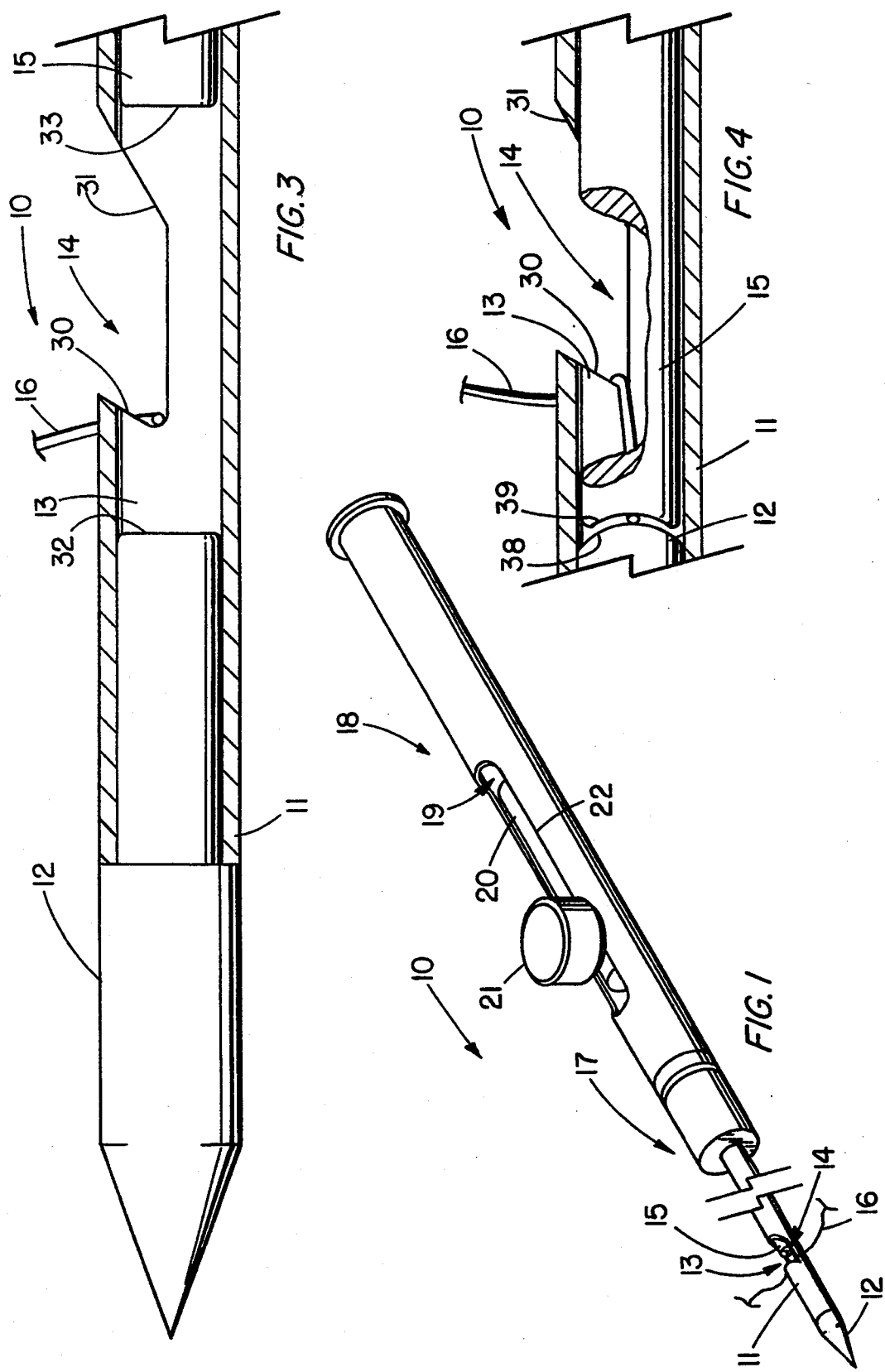

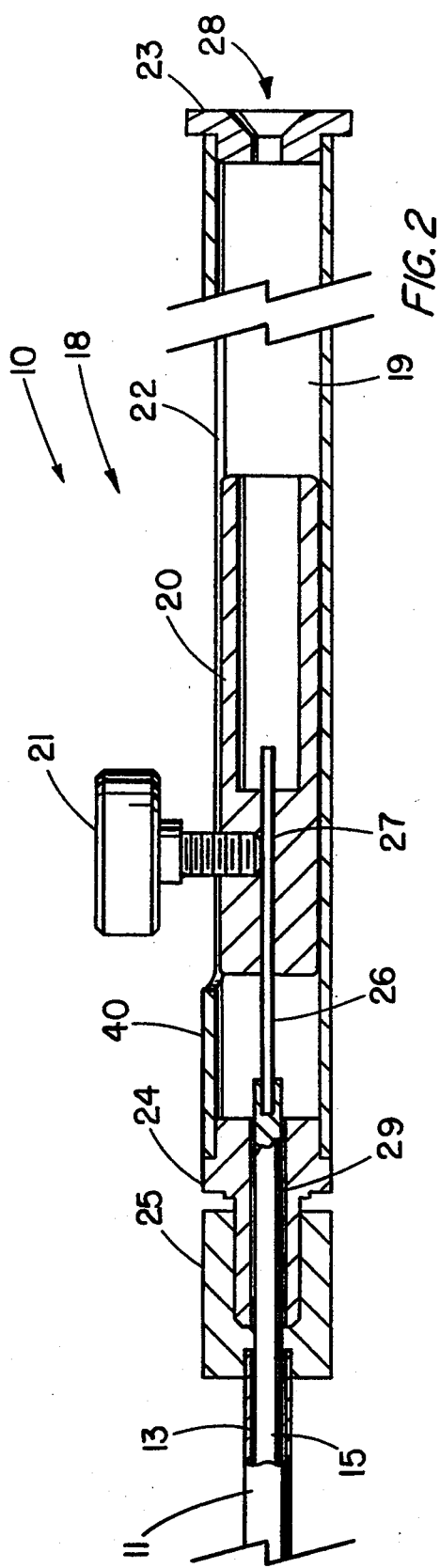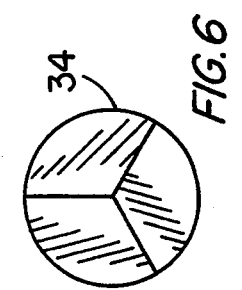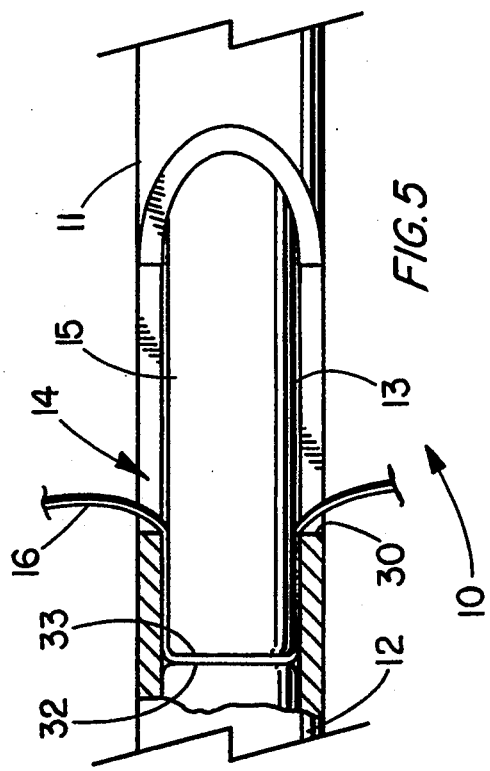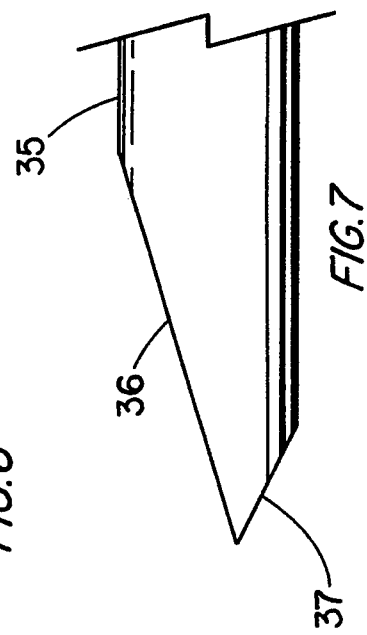

SUTURE DRIVER

TECHNICAL FIELD

This invention relates generally to surgical instruments and, in particular, to an instrument for manipulating sutures at a surgical site.

BACKGROUND OF THE INVENTION

During endoscopic procedures, sutures are commonly introduced to the interior of the body of a patient with a knot pushing rod and removed therefrom with the aid of grasping forceps and scissors. The use of these known devices requires an access sheath or entry site in addition to the access sheath used by a surgeon for visualization or insufflation of the body cavity. To provide secondary access, a puncture is formed using a trocar needle, the puncture is dilated, and a sheath is positioned in the puncture through the abdominal wall. Providing additional access sites results in the increased duration of the procedure as well as the risk of complications to the patient.

An approach to removing a suture from the interior of the body of a patient is to use a combination subcutaneous suture probe. The probe includes an outer cutting tube, an inner hollow tube with a crochet-type hook positioned in the distal end thereof, and an inner clamping rod. The probe is positioned through the abdominal wall and into infected sinuses for probing and locating a loop of suture. The probe is pulled against the loop for positioning the suture thread in the crochet hook of the inner hollow tube. The inner clamping rod secures the suture therein. Then the outer cutting tube is advanced distally for cutting the suture thread on one side of the crochet hook. The suture thread remains grasped within the crochet hook of the device for removal from the body. A problem with the crochet hook and inner clamping rod of the probe is that the suture can be readily pulled from between the clamping surfaces thereof when attempting to pull on the suture and encountering any resistance therefrom. Another problem with the use of this probe is that the suture thread can be inadvertently cut on both sides of the crochet hook with the outer cutting tube. As a result, only a small piece of suture thread would remain within the device, leaving a length of suture extending from the abdominal tissue. Furthermore, with the suture thread already cut, no loop of suture remains for the probe to engage and pull into the crochet hook. Still another problem is that the inner hollow tube with the crochet-type hook can be bent during percutaneous insertion since the inner clamping rod does not extend through the hook and reinforce the hollow tube.

Another approach to introducing suture to the interior of the body of a patient and removing suture therefrom is the use of a suture threading, stitching, and wrapping device. The device includes a tissue clamping bracket and a shaft with a pointed front end and a hook directly behind the front end. In use, the U-shaped tissue clamping bracket positions a suture thread behind a mass of tissue. Then the pointed front end of the shaft penetrates the tissue mass for positioning the suture thread into the hook. The shaft is pulled proximally for drawing the suture thread through the tissue mass and into an outer tube. A problem with the use of this device is that it is introduced into the body of a patient via an access sheath or skin portal. Again, providing an additional access site results in the increased duration of the procedure as well as the risk of complications to the patient. Another problem with the use of this device is that the suture thread is positioned in the device by tensioning the suture thread. Suture thread can be inadvertently released from the device and, as a result, failed attempts to introduce suture into the body or remove suture therefrom can occur. Yet another problem with the use of this device is that suture thread can be inadvertently cut when drawing the shaft into the outer tube, if the tolerance between the shaft and tube is close enough to prevent release of the suture thread from the device. Conversely, the suture inadvertently slips out of the hook if the tolerance between the shaft and outer tube is far apart.

SUMMARY OF THE INVENTION

The foregoing problems are solved and a technical advance is achieved in an illustrative suture driver for securely clamping a suture in a hollow passage and recessed channel thereof and manipulating the suture to or from a surgical site. Advantageously, the suture driver includes a pointed distal end for percutaneously delivering the suture to the surgical site without the need of a surgical access sheath. The suture driver includes an outer elongated member tube having a hollow passage extending longitudinally therein. The outer member tube has a recessed channel that is positioned proximal the closed distal end of the passage and communicates exterior to the outer member tube and with the hollow passage. The driver also includes an inner, elongated member rod that passes through the recessed channel and reinforces the distal end of outer member tube during percutaneous introduction into a patient. The inner member rod also advantageously has a position for securely clamping the suture in the hollow passage and the recessed channel when the inner member rod is positioned adjacent the closed distal end of the outer member tube and through the recessed channel. Advantageously, the suture is not only clamped between the clamping surfaces of the inner member rod and closed distal end of the outer member tube, but is also captured between the surface of the inner member rod and the inner surface of the outer member tube. Furthermore, the suture also engages the edges of the distal portion of the recessed channel, thus advantageously establishing additional engagement points to securely position the suture in the driver when manipulating the suture to and from the surgical site.

The suture driver also comprises a handle that is attached to the proximal end of the outer member tube and has a chamber therein communicating with the hollow passage of the outer member tube. The handle further includes a piston that is movably positioned in the chamber and removably attached to the inner member rod. The handle also has a slot extending longitudinally therealong through which a thumb screw laterally extends from the piston and through the slot for movement of the inner member rod to the clamping position. The piston of the handle includes a passage for receiving the proximal end of the inner member rod. The thumb screw threadably and selectively engages the proximal end of the inner member rod when the rod is positioned in the passage of the piston.

To facilitate capture of the suture, the recessed channel includes an undercut distal portion and a beveled proximal portion for positioning the suture distally in the channel. The closed distal end of the passage includes a pointed distal end for penetrating tissue. The closed distal end also has a clamping surface facing the hollow passage of the outer member tube. The inner member rod includes a second clamping surface facing the clamping surface of the closed distal end when positioned in the hollow passage of the outer member tube. The suture is advantageously clamped between these two surfaces when the clamping surface of the inner member rod is positioned adjacent the clamping surface of the closed distal end when the inner rod is also positioned through the recessed channel.

BRIEF DESCRIPTION OF HE DRAWING

FIG. 1 depicts pictorial view of an illustrative embodiment of the suture driver of the present invention;

FIG. 2 depicts a partially sectioned and enlarged side view of the handle of the suture driver of FIG. 1;

FIG. 3 depicts a partially sectioned and enlarged side view of the distal end of the suture driver of FIG. 1;

FIG. 4 depicts a partial view of the suture driver of FIG. 3 with the inner member rod in a clamping position;

FIG. 5 depicts a partial top view of the suture driver of FIG. 3 in a clamping position;

FIG. 6 depicts an end view of the closed distal end of the suture driver of the present invention with an alternative, trocar shape; and FIG. 7 depicts a partial side view of the closed distal end of the suture driver of the present invention with an alternative, beveled shape.

DETAILED DESCRIPTION

FIG. 1 depicts a pictorial view of an illustrative embodiment of suture driver 10 for clamping suture 16 in hollow passage 13 and recessed channel 14 thereof and manipulating the suture to and from a surgical site. The suture driver includes an outer, elongated member tube 11 with inner elongated member rod 15 slidably positioned in hollow passage 13 of the outer tube. Outer member tube 11 has a closed and pointed distal end 12 for puncturing tissue and percutaneously positioning a suture and/or the distal end of the driver at the surgical site. For example, after percutaneous introduction into a patient, the suture driver is used to clamp and pull a suture internally from the body of a patient in such procedures as a periurethral suspension. When advancing or introducing the suture driver into tissue, the rigid, inner member rod is advanced to the distal end of the suture driver for supporting and reinforcing the outer member tube. Positioned proximal the closed distal end of hollow passage 13, recessed channel 14 is transversely positioned through the outer member tube to communicate exterior to the outer member tube and with the hollow passage.

Suture driver 10 also includes handle 18 that is attached to proximal end 17 of the outer member tube for manual manipulation of the suture driver by the attending physician. The handle includes chamber 19 extending longitudinally therein and communicating with hollow passage 13 of the outer member tube. The handle also includes piston 20 that is removably attached to the proximal end of the inner member rod with thumb screw 21. Thumb screw 21 laterally extends from piston 20 through slot 22 that extends longitudinally along the handle. The longitudinal slot permits communication with the chamber and the exterior of the handle. The piston also is slidably positioned in the chamber with the thumb screw for movement of the inner member rod to a position for clamping the suture between the clamping surfaces of the closed distal end and the inner member rod.

FIG. 2 depicts a partially sectioned and enlarged side view of handle 18 of suture driver 10 of FIG. 1. Handle 18 comprises an aluminum tube 40 approximately 4.5" long with an outside diameter of approximately 0.375" and an inside diameter of approximately 0.245". Longitudinal slot 22 is approximately 2" long and approximately 0.187" wide with the proximal end positioned approximately 0.5" from the proximal end of the tube. The proximal end of the handle includes a proximal end cap 23 glued in passage 19 of the handle tube. The proximal end cap also includes passage 28 to facilitate cleaning and sterilization of the reusable handle. Externally threaded distal through cap 24 is glued into the distal end of the handle tube. Through cap 24 includes passage 29 for passing inner member rod 15 therethrough. Outer tube 11 includes internally threaded hub 25 attached to the proximal end thereof with, for example, silver solder, for threadably attaching the proximal end of outer tube 11 to through cap 24 and the distal end of the handle. Hub 25 is approximately 0.490" long with a 0.375" outside diameter. A plurality of ¼-32 threads is formed inside the hub from the proximal end thereof to a depth of 0.350". Adjacent the plurality of threads, an inside diameter of 0.070" extends for a length of 0.040", and a 0.112" inside diameter extends to the distal end for a length of 0.100" to seat and solder the proximal end of the outer member tube. As a result, chamber 19 communicates with hollow passage 13 of the outer member tube via cap passage 29.

Chrome-plated brass piston 20, with passage 27 extending longitudinally therethrough, is slidably positioned in handle chamber 19. A reduced diameter extension rod 26 is attached to the proximal end of inner member rod 15 using, again, for example, silver solder. The inner member rod extension is inserted into piston passage 27 and selectively engaged with thumb screw 21 threadably inserted into the piston passage. The diameter of the proximal portion of piston passage 27 is enlarged to lighten the weight of the piston and to facilitate cleaning of the handle components. Piston 20 is approximately 1.500" long with an outside diameter of approximately 0.232". Piston passage 27 has a diameter of approximately 0.046" about the distal end of the piston, whereas the proximal portion of the piston passage diameter is enlarged to approximately 0.125".

FIG. 3 depicts a partially sectioned and enlarged side view of the distal end of suture driver 10 with recessed channel 14 open for receiving suture 16. Closed and pointed distal end 12 is positioned in hollow passage 13 at the distal end of outer member tube 11 with clamping surface 32 at the proximal end of pointed end plug 12 facing proximally into hollow passage 13. Inner member rod 15 with clamping surface 33 thereof facing clamping surface 32 is positioned in hollow passage 13 proximal to recessed channel 14. With the inner member rod slidably removed from recessed channel 14, suture 16 is positioned into undercut distal portion 30 of the channel. Recessed channel 14 also includes beveled proximal portion 31 for guiding the suture distally downward and into undercut distal portion 30.

FIG. 4 depicts a partial view of suture driver 10 of FIG. 3 in a position for clamping suture 16 in hollow passage 13 and recessed channel 14. Distal end plug 12 includes cylindrically convex clamping surface 38, and inner member rod 15 includes oppositely facing cylindrically concave clamping surface 39. Clamping surfaces 38 and 39 are alternative embodiments of blunt clamping surfaces 32 and 33, respectively. Clamping surface 39 of inner member rod 15 engages and centers suture 16 against oppositely facing clamping surface 38 of closed distal end plug 12. Undercut distal portion 30, as well as cylindrically concave clamping surface 39 and cylindrically convex clamping surface 38, also facilitates the central positioning of suture 16 in hollow passage 13.

FIG. 5 depicts a partially sectioned, top view of suture driver 10 of FIG. 3 with inner member rod 15 in a clamping position and extending distally through recessed channel 14. Suture 16 is engaged by clamping surface 33 of the inner member rod and oppositely facing clamping surface 32 of the closed distal end plug. Distal to recessed channel 14, suture 16 is further maintained in hollow passage 13 by engagement longitudinally between the outer longitudinal surface inner member rod 15 and the inner surface of outer member tube 11. The free ends of suture 16 extend transversely from recessed channel 14 at undercut distal portion 30 thereof. As a result, the suture makes three or more bends with the driver in the clamped position to further secure the suture in the driver.

As depicted in the preferred embodiment of suture driver 10, outer member tube 11 comprises, for example, a 7.780" length of 12 gauge heavy wall stainless steel tube with a 0.109" outside diameter and 0.077" inside diameter. Recessed channel 14 is approximately 0.055" deep and 0.750" long overall. Beveled proximal portion 31 extends along the axis of the tube for a length of 0.100". Undercut distal portion 30 extends along the axis of the tube for a length of 0.030" and includes a 0.0750" radius at the bottom of the channel. Recessed channel 14 extends intermediately between portions 31 and 32 for a length of 0.150". Undercut distal portion 30 of the recessed channel is formed 0.300" back from the distal end of outer member tube 11. Pointed and closed distal end plug 12 comprises, for example, a 0.565" length of a cylindrical stainless steel rod with a maximum outside diameter of 0.109" extending for a length of 0.200". The conically shaped distal point extends 0.135" along the axis of the plug at a 20 degree angle. The plug includes a minimum outside diameter of 0.073" for a length of 0.230". The edges adjacent clamping surface 33 are smoothed. Inner member rod 15 is a 8.00" length of stainless steel with a 0.068" outside diameter and a 0.100" long, 0.043" diameter hole drilled at the proximal end and along the centerline thereof. Inner rod extension 26 is a 1.100" long, 0.041" diameter piece of stainless steel fixedly positioned in the hole of the inner member rod using solder.

FIGS. 6 and 7 depict alternate shapes for the closed and pointed distal end of the suture driver of the present invention. FIG. 6 depicts an end view of closed distal end 34 with a trocar-shaped point. Trocar-shaped distal end 34 cuts a cylindrical hole in tissue during use. In contrast, conically shaped, closed distal end 12 of FIG. 3 makes a tiny puncture and subsequently dilates tissue during advancement of the suture driver.

FIG. 7 depicts a partial side view of closed distal end 35 with primary bevel 36 extending longitudinally therealong at, for example, a 17 degree angle to the centerline of the closed distal end. On the opposite side of closed distal end 35, secondary bevel 37 extends longitudinally therealong at an approximately 27 degree angle. The secondary bevel provides increased sharpness to closed distal end 35. Beveled, closed distal end 35 cuts a slit-like opening in tissue during use.

It is to be understood that the above-described suture driver is merely an illustrative embodiment of the principles of this invention and that other suture drivers may be devised by those skilled in the art without departing from the spirit and scope of this invention. In particular, a hole extending transversely through the outer member tube can be substituted for the recessed channel. The suture driver can also be made with other materials such as plastics or other metals depending on whether the instrument will be reused or used only one time. The outer member tube and inner rod can be made for onetime use in conjunction with a reusable handle.

What is claimed is:

1. A suture driver comprising:
an outer, elongated member having a hollow passage extending longitudinally therein, said hollow passage including a closed distal end, said outer member also having a recessed channel positioned proximal said closed distal end of said hollow passage and communicating with said hollow passage and an exterior to said outer member; and
an inner, elongated member having a position in said hollow passage of said outer member adjacent said closed distal end and distal said recessed channel for clamping a suture in said recessed channel and said hollow passage distal said recessed channel.

2. The suture driver of claim 1 further comprising a handle attached to a proximal end of said outer member and having a chamber therein communicating with said hollow passage of said outer member.

3. The suture driver of claim 2 wherein said handle further includes a piston movably positioned in said chamber and removably attached to said inner member.

4. The suture driver of claim 3 wherein said handle has a slot extending longitudinally therealong and communicating with said chamber and the exterior and wherein said piston includes a lateral member extending through said slot to the exterior for movement of said inner member to said position for clamping.

5. The suture driver of claim 4 wherein said lateral member includes a thumb screw selectively engaging said inner member.

6. The suture driver of claim 5 wherein said piston includes a passage therein for receiving a proximal end of said inner member and wherein said thumb screw threadably and selectively engages said proximal end of said inner member when positioned in said passage of said piston.

7. The suture driver of claim 1 wherein said recessed channel includes an undercut distal portion.

8. The suture driver of claim 1 wherein said recessed channel includes a beveled proximal portion.

9. The suture driver of claim 1 wherein said closed distal end is pointed.

10. The suture driver of claim 1 wherein said closed distal end has a predetermined shape.

11. The suture driver of claim 10 wherein said predetermined shape is a cone shape.

12. The suture driver of claim 1 wherein said closed distal end includes and presents a first clamping surface to said hollow passage.

13. The suture driver of claim 12 wherein said inner member in said hollow passage of said outer member includes a second clamping surface facing said first clamping surface of said closed distal end.

14. The suture driver of claim 1 wherein said recessed channel includes an undercut distal portion for engagement of a suture.

15. A suture driver comprising:
   an outer tube having a hollow passage extending longitudinally therein; a closed, pointed distal end; a first clamping surface positioned proximate said closed distal end in said hollow passage; and a recessed channel positioned proximal said first clamping surface and communicating with said hollow passage and an exterior to said outer tube; and
   an inner rod having a second clamping surface and a position in said hollow passage distal said recessed channel for clamping a suture in said hollow passage distal said recessed channel between said first and said second clamping surfaces.

16. The suture driver of claim 15 wherein said recessed channel includes an undercut distal portion for engagement of a suture when positioned therein.

17. The suture driver of claim 16 further comprising a handle attached to a proximal end of said outer tube and having a chamber therein communicating with said hollow passage of said outer tube.

18. The suture driver of claim 17 wherein said handle has a slot extending longitudinally therealong communicating with said chamber and the exterior and includes a piston movably positioned in said chamber and removably attached to said inner rod and wherein said piston includes a lateral member extending through said slot to the exterior for movement of said piston in said chamber.

19. The suture driver of claim 18 wherein said piston includes a passage therein for receiving a proximal end of said inner rod and wherein said thumb screw selectively engages said proximal end of said inner rod in said passage of said piston.

20. A suture driver comprising:
   an outer tube having a hollow passage extending longitudinally therein; a closed, pointed distal end; a first clamping surface positioned proximate said closed distal end in said hollow passage; and a recessed channel positioned proximal said first clamping surface, communicating with said hollow passage and an exterior to said outer tube, and having a beveled proximal portion and an undercut distal portion for engagement of a suture when positioned therein;
   an inner rod including a second clamping surface positioned in said hollow passage facing said first clamping surface, said inner rod having a position for clamping a suture in said hollow passage distal said recessed channel between said first and said second clamping surfaces; and
   a handle attached to a proximal end of said outer tube and having a chamber therein communicating with said hollow passage of said outer tube and a piston movably positioned in said chamber and removably attached to a proximal end of said inner rod, a slot extending longitudinally along said handle and communicating with said chamber and the exterior, said piston including a thumb screw extending laterally through said slot and engaging said proximal end of said inner rod.

* * * * *